United States Patent [19]

Minagawa et al.

[11] Patent Number: 5,667,996
[45] Date of Patent: Sep. 16, 1997

[54] PROCESS FOR PRODUCTION OF BACTERIAL CELLS CONTAINING POLY-3-HYDROXY BUTYRIC ACID

[75] Inventors: Shunichiro Minagawa; Shigeki Imagawa; Iwao Terao; Torakazu Tahara, all of Niigata, Japan

[73] Assignee: Mitsubishi Gas Chemical Company, Inc., Tokyo, Japan

[21] Appl. No.: 507,576

[22] Filed: Jul. 26, 1995

Related U.S. Application Data

[63] Continuation-in-part of Ser. No. 298,428, Aug. 30, 1994, abandoned.

[30] Foreign Application Priority Data

Sep. 10, 1993 [JP] Japan .................. 5-225899
Oct. 6, 1993 [JP] Japan .................. 5-250674
Oct. 6, 1993 [JP] Japan .................. 5-250675

[51] Int. Cl.⁶ .................. C12P 7/44; C12P 7/42; C12P 7/02
[52] U.S. Cl. .................. 435/146; 435/132; 435/141; 435/143; 435/144; 435/145; 435/170; 435/155; 435/142; 435/136
[58] Field of Search .................. 435/142, 132, 435/146, 155, 170, 143, 144, 145

[56] References Cited

U.S. PATENT DOCUMENTS

| 4,336,334 | 6/1982 | Powell et al. | 435/146 |
| 5,135,859 | 8/1992 | Witholt et al. | 435/135 |
| 5,302,525 | 4/1994 | Groleau et al. | 435/252.1 |

*Primary Examiner*—Blaine Lankford
*Attorney, Agent, or Firm*—Klauber & Jackson

[57] ABSTRACT

Disclosed is a process for accumulating a poly-3-hydroxy butyric acid in bacterial cells by continuously fermenting a methanol-assimilating bacterium having a capability of producing a poly-3-hydroxy butyric acid, in a single fermentation vessel by using methanol as carbon source at a limited feeding rate of nitrogen, phosphorus, or potassium such that the retention time for the fermentation is more than 10 hours.

4 Claims, No Drawings

PROCESS FOR PRODUCTION OF BACTERIAL CELLS CONTAINING POLY-3-HYDROXY BUTYRIC ACID

This is a continuation-in-part application of U.S. patent application Ser. No. 08/298,428 filed Aug. 30, 1994 now abandoned.

BACKGROUND OF THE INVENTION

(1) Field of the Invention

The present invention relates to a process for producing a poly-3-hydroxy butyric acid (hereinafter referred to as PHB).

More particularly, the present invention is addressed to a single stage continuous fermentation process for the production of bacterial cells containing a poly-3-hydroxy butyric acid.

(2) Description of the Related Art

PHB is produced and accumulated as an energy storage substance in bacterial cells of a large number of microorganisms. Since PHB is a thermoplastic polymer exhibiting an excellent biodegradability and biocompatibility, it has attracted attention as a "clean" plastic which does not destroy environment.

Also, PHB has been expected for many years to apply in various fields including biomedical materials such as surgical threads and fracture braces, and gradually releasing systems where a drag or pesticide is gradually released to environment.

Particularly, since synthetic plastics have caused serious public problems from the standpoint of environmental pollution as well as resource circumstances in recent years, PHB has been watched with an interest as a biopolymer which does not rely upon petroleum.

Heretofore, several processes for producing PHB have been proposed in Unexamined Japanese Patent Publication Nos. 60-214888 and 60-251889, and Examined Japanese Patent Publication Nos. 02-20238 and 03-65154.

The Examined Japanese Patent Publication No. 02-20238 has disclosed a process for the production of PHB by continuously fermenting bacterial cells of a genus of Alcaliqenes by using glucose as a source of carbon (hereinafter may be referred to as substrate) under a condition of restricted growth by limiting the feeding of nitrogen or phosphorus.

The Unexamined Japanese Patent Publication No. 60-214888 and Examined Japanese Patent Publication No. 03-65154 have disclosed processes for producing PHB by fermenting bacterial cells of a genus of Azotobacter or Protomonas in a batch method under a condition of restricted growth similar to that used for the genus of Alcaliqenes.

However, these processes are unsatisfactory in commercial production of PHB due to their high production cost. Further, those processes have such a defect that the production cost of PHB can not be brought to a low level since a main nutrient used for growing bacterial cells, namely, a carbon source is expensive, that the accumulation of PHB by a continuous fermentation is insufficient, or that the production process is complicated since two stages fermentations are required.

The cost of a raw material (that is, a substrate) is an important factor in the total cost for the production of PHB. While the processes for the production of PHB using glucose or saccharose as a raw material are described in the Examined Japanese Patent Publication No. 02-20238 and Unexamined Japanese Patent Publication No. 60-214888, the increase in the production cost of PHB can not be avoided in these processes.

A fermentation process by using inexpensive methanol as a substrate is described, for instance, in Unexamined Japanese Patent Publication No. 56-117793 where a microorganism of a species of *Methylobacterium organophilum* is continuously fermented using methanol as a substrate in a first fermentation vessel (fermenter) without the limitation of a nutrient. At this stage, the accumulation of PHB in cells will not be taken place. Then, the microorganism is continuously transferred to a second fermentation vessel in which the microorganism is subjected to further fermentation using nitrogen or phosphorus as a limiting factor for growth. At this stage, PHB is accumulated in cells for the first time. According to the description in the specification of Unexaminated Japanese Patent Publication No. 56-117793, however, the content of PHB is only 25 to 47% by weight based on the weight of dried cells.

The process where two stages fermentations are undertaken by using two fermentation vessels in a series has such defects that the process is complicated and that a satisfactory PHB content can not be obtained.

Further, while it is described in the Examined Japanese Patent Publication No. 02-20238 that a strain of *Methylobacterium organophilum* NCIB 11483 was continuously fermented with methanol as a substrate under nitrogen limitation, the maximum PHB content achieved under the conditions in the Publication No. 02-20238 was as low as about 11%.

SUMMARY OF THE INVENTION

An object of the present invention is to solve the problems in the conventional processes mentioned above and to provide a process for the production of PHB in a large quantity and more stably at a low production cost by a continuous fermentation by using a bacterium which can assimilate inexpensive methanol.

Other objects of the present invention will be apparent to those skilled in the art from the following detailed description and appended claims.

As a result of the study by the present inventors on a process for the production of PHB at a low production cost, we found the following advanced fermenation process using a methanol-assimilating baceterium with a capability of producing PHB. Namely, it has been found that PHB can be accumulated in a large quantity concurrently with the growth of the bacterium, by making the growth rate very slow compared with the generation time of a bacterium in the case where a limiting factor for the growth rate does not exist, in other words, by making a retention time very long, when growing the bacterium in a single fermentation vessel at a restricted growth by limiting the feeding rate of nitrogen, phosphorus, or potassium, in other words, when a continuous fermentation is undertaken under the condition that a limiting factor for the growth rate of the bacterium is nitrogen, phosphorus, or potassium.

That is, the present invention is concerned with a process for the production of PHB by continuously fermenting a methanol-assimilating bacterium by using methanol as a source of carbon to accumulate PHB in cells of the bacterium and obtaining PHB from the bacterial cells characterized in that the feeding rate of nitrogen, phosphorus, or potassium is limited so that a retention time in a single fermentation vessel is extended to more than 10 hours.

DESCRIPTION OF THE PREFERRED EMBODIMENTS

In the present invention, PHB is a polyester composed of a repeating unit of —OCH(CH$_3$)CH$_2$CO—.

In the present invention, a bacterium having both a capability of producing PHB and a methanol-assimilating property can satisfactorily be used. The bacterium include, for example, a genus of Protomonas, Methylobacterium, Xanthobacter, Hyphomicrobium, Paracoccus, Methylobacillus, and Ancylobacter.

The source of nitrogen in the fermentation is not particularly restricted provided that it can be assimilated by the bacterium to be used. The nitrogen source includes ammonia, Urea, nitric acid, a substance containing an organic nitrogen, for example, yeast extract, and malt extract.

As the source of phosphorus used in the fermentation, for example, phosphoric acid and a phosphate can be used. The phosphate includes, for example, a potassium salt, sodium salt, and ammonium salt.

As the source of potassium in the fermentation, for example, caustic potash and a potassium salt can be used. The potassium salt includes, for example, a sulfate, phosphate, and nitrate.

As other inorganic salts necessary for the fermentation, metal salts such as salts of sodium, magnesium, iron, calcium, zinc, manganese, cobalt, copper, and molybdenum can be used.

While conditions for the fermentation are different depending upon the strain to be used, its temperature is generally 25° to 40° C. and preferably 30° to 38° C. In many cases, the optimum temperature for obtaining an excellent PHB productivity is varied depending upon the strain.

The pH for the fermentation is usually 5 to 8 and preferably 6.0 to 7.5.

The strain is aerobically fermented, it is aerated with air or oxygen during the fermentation, and the fermentation medium is stirred to efficiently dissolve the oxygen into the medium, as necessary. The concentration of oxygen dissolved in the fermentation solution is preferably higher than 0.3 ppm under usual conditions.

The fermentation vessel can be used of any form provided that it is an aeration type mixing vessel. Thus, for example, a mechanical stirring vessel, air-lift type fermentation vessel, and bubble tower type fermentation vessel can be employed.

The components of the fermentation medium such as a carbon source, a nitrogen source, and various kinds of inorganic salts and additives can be fed or supplied collectively or individually, and continuously or intermittently. For instance, methanol can be supplied to a fermentation vessel as a mixture with other components of the medium, or can be supplied to the vessel separately from other components.

The pH of the fermentation broth can be controlled with ammonia when the fermentation is undertaken or carried out by a method where the feeding of phosphorus or potassium is limited. When the condition under which the feeding of nitrogen is limited is adopted in the fermentation of the present invention, the pH is preferably controlled with a base not containing nitrogen, for example, caustic soda and caustic potash.

In order to accumulate PHB, a method is usually employed where an element of the fermentation medium other than the carbon source is limited. Thus, it is preferable to limit the feeding of the component such as nitrogen, phosphorus, sulfur, potassium, or trace elements, for example, manganese, zinc, and copper. In the process of the present invention, feeding of nitrogen, phosphorus, or potassium is limited.

The fermentation methods used in the present invention are explained in detail in the following for each component to be limitedly supplied:

[Fermentation method where feeding of nitrogen is limited]

Nitrogen is conveniently fed as an ammonium salt or gaseous ammonia or aqueous ammonia. For instance, when the gaseous ammonia or aqueous ammonia is fed as a nitrogen source, a method is used where a constant amount of gaseous or aqueous ammonia is continuously fed separately from other components of the fermentation medium which are also continuously fed.

When the nitrogen source is fed as an ammonium salt, it can be fed together with other components of the fermentation medium after the ammonium salt was dissolved in the medium. Thus, a fermentation method is used where the amount of the nitrogen source is reduced to less than the amount required for bacterial cells to actively grow, namely, the feeding rate of nitrogen is limited such that the nitrogen feeding rate is a limiting factor for the growth of bacterial cells.

Determination of the concentration of residual nitrogen in the fermentation broth is continuously carried out by a conventional method using an ammonium ion electrode or ion chromatography, as the concentration of ammonium ion, when ammonia or ammonium compound is used as a nitrogen source (Determination is possible down to 1 ppm). According to the fermentation method of the present invention, the amount of ammonium ion becomes such a small amount that ammonium ion can not be detected substantially. However, when the mixing property of the fermentation broth is bad, the concentration of residual ammonium ion in the fermentation broth may show a few ppm in partial.

As a method for keeping a stationary state in a continuous fermentation system, a method using the so-called substrate-limiting fermentation is generally adopted where the fermentation is carried out while limiting the feeding rate of a substrate from the standpoint of substrate saving. However, the fermentation method of the present invention is different from the conventional substrate-limiting fermentation, and the method of the present invention is a nitrogen-limiting fermentation method where the fermentation is carried out while keeping a stationary state by limiting the feeding rate of nitrogen to a fermentation vessel, and thus a growth limiting factor is only nitrogen.

After the fermentation was switched to a continuous fermentation of the present invention, the feeding of the nitrogen source is controlled such that the concentration of residual ammonium ion in the fermentation broth is decreased to such a low level that the amount of ammonium ion can not be detected by an ion analyzer usually employed. At the same time, the feeding amount of the fermentation medium or methanol is adjusted such that the concentration of residual methanol in the fermentation broth is constant. In the production in a commercial scale, the feeding amount of methanol and fermentation medium is automatically adjusted by determining the concentration of residual methanol with the passage of time with an analyzer such as a gas chromatography, and feeding back the signals from the analyzer to the feeding system of the methanol or medium.

The concentration of methanol in the fermentation solution is maintained usually about 10 to about 3,000 ppm and preferably about 200 to about 2,000 ppm.

The concentration of the residual methanol can also be found by determining the amount of methanol in a fermentation waste gas with an analyzer such as a hydrocarbon analyzer or a gas chromatography.

Thus, a stationary state in the fermentation can be obtained under a constant aeration condition, and it is only nitrogen which restrict the growth of a bacterium under the stationary state.

While the concentration of bacterial cells in the fermentation broth (based on the weight of dried bacterial cells, the same base will be used hereinafter) of a continuous fermentation of the present invention is not particularly restricted, it is usually 10 to 100 g/l. The preliminary fermentation is shifted to a continuous fermentation of the present invention after the concentration of bacterial cells of the preliminary fermentation reached about the same concentration as that of bacterial cells at a stationary state of the present invention or slightly lower concentration.

The growth rate of a bacterium can be arbitrarily varied by adjusting the feeding rate of nitrogen. That is, in order to increase the growth rate (to shorten the retention time), conditions which increase the feeding rate of nitrogen can be satisfactorily selected. Conversely, in order to reduce the growth rate (to increase the retention time), conditions which decrease the feeding rate of nitrogen can be acceptably selected.

Prior to a continuous fermentation to be conducted under a limitation of nitrogen feeding rate in the present invention, a preliminary fermentation is undertaken where a bacterium is actively grown until the concentration of the bacterial cells in the fermentation broth reaches a prescribed value. The preliminary fermentation means the fermentation which gives an active fermentation broth having an applicable cell concentration for the continuous fermentation of the present invention to be conducted subsequently. Any fermentation method which is publicly known can be used for preliminary fermentation.

The preliminary fermentation includes, for example, a batch fermentation where a fermentation is undertaken while feeding a sufficient amount of a substrate, other components of the fermentation medium, and oxygen; another batch fermentation where fermentation is undertaken while limiting the feeding of only nitrogen; and a continuous fermentation where a continuous fermentation is undertaken while feeding a sufficient amount of a substrate, other components of the fermentation medium, and nitrogen, following such a batch fermentation as mentioned above.

The preliminary fermentation can be undertaken by a usual method, and fermentation temperature, pH, type of substrate, components of the fermentation medium, concentration of a substrate in the medium or fermentation broth are the same as those in a continuous fermentation of the present invention.

Following the preliminary fermentation, a continuous fermentation described above where the feeding rate of nitrogen is limited can be carried out.

The content of PHB in bacterial cells increases as the feeding rate of nitrogen is reduced and the retention time in a fermentation vessel is extended. When the retention time is chosen to be more than 15 hours, a great increase in the content of PHB is observed. To make the retention time more than 15 hours, the feeding molar ratio of carbon atom to nitrogen atom (C/N ratio) is usually adjusted to more than 10. The carbon atom of C/N ratio is derived from methanol and the nitrogen atom of C/N ratio is derived from nitrogen source such as ammonia.

[Fermentation method where feeding of phosphorus is limited]

In a fermentation method where the feeding of phosphorus is limited, fermentation is undertaken while keeping a stationary state by limiting the feeding rate of phosphorus to a fermentation vessel. Thus, in this method, a factor which limit the growth of a bacterium is only phosphorus.

While the source of phosphorus is generally fed by mixing it with other components of the fermentation medium which are continuously fed, it can also be fed continuously at a constant rate separately from other components of the medium.

Thus, a fermentation is undertaken where the amount of a phosphorus source is reduced to an amount less than that necessary for bacterial cells to actively grow, namely, the feeding rate of phosphorus is limited such that the phosphorus feeding rate is a limiting factor for the growth of bacterial cells.

The concentration of residual phosphorus in the fermentation broth is continuously determined by a conventional method using an ion chromatography as the concentration of phosphoric acid ion (Detection is possible down to 1 ppm). According to the method of the present invention, the concentration of residual phosphorus can be reduced to such a low level that the phosphorus ion can not be detected substantially. However, when the mixing property of the fermentation broth is bad, the concentration of residual phosphoric acid ion in the fermentation solution may show a few ppm in partial.

After the fermentation was switched to a continuous fermentation of the present invention, the feeding of the phosphorus source is controlled such that the concentration of residual phosphoric acid ion in the fermentation broth is decreased to such a low level that the amount of phosphoric acid ion can not be detected by an ion analyzer usually employed. At the same time, the feeding amount of the fermentation medium or methanol is controlled such that the concentration of residual methanol in the fermentation broth is constant. In the production in a commercial scale, the feeding amount of methanol and fermentation medium is automatically adjusted by determining the concentration of residual methanol with the passage of time with an analyzer such as a gas chromatography, and feeding back the signals from the analyzer to the feeding system of the methanol or medium.

The concentration of residual methanol in the fermentation broth is maintained usually about 10 to about 3,000 ppm and preferably about 200 to about 2,000 ppm.

The concentration of the residual methanol can also be found by determining the amount of methanol in a fermentation waste gas with an analyzer such as a hydrocarbon analyzer or a gas chromatography.

Thus, a stationary state in the fermentation can be obtained under a constant aeration condition, and it is only phosphorus which restrict the growth of a bacterium under the stationary state.

While the concentration of bacterial cells in the fermentation broth of a continuous fermentation of the present invention is not particularly restricted, it is usually 10 to 100 g/l. The preliminary fermentation is shifted to a continuous fermentation of the present invention after the concentration of bacterial cells of the preliminary fermentation reached about the same concentration as that of bacterial cells at a stationary state of the present invention or slightly lower concentration.

The growth rate of a bacterium can be arbitrarily varied by adjusting the feeding rate of phosphorus. That is, in order to increase the growth rate (to shorten the retention time), conditions which increase the feeding rate of phosphorus can be satisfactorily selected. Conversely, in order to reduce the growth rate (to increase the retention time), conditions which decrease the feeding rate of phosphorus can be acceptably selected.

Prior to a continuous fermentation conducted under a limitation of phosphorus feeding rate in the present invention, a preliminary fermentation is undertaken where a bacterium is actively grown until the concentration of bacterial cells in the fermentation broth reaches a prescribed value.

The preliminary fermentation includes, for example, a batch fermentation where a fermentation is undertaken while feeding a sufficient amount of a substrate, other components of the fermentation medium, and oxygen; another batch fermentation where fermentation is undertaken while limiting the feeding of only phosphorus; and a continuous fermentation where a continuous fermentation is undertaken while feeding a sufficient amount of a substrate, other components of the fermentation medium, and phosphorus, following such a batch fermentation as mentioned above.

The preliminary fermentation can be undertaken by a usual method, and fermentation temperature, pH, type of substrate, components of the fermentation medium, concentration of a substrate in the medium or fermentation broth are the same as those in a continuous fermentation of the present invention.

Following the preliminary fermentation, the continuous fermentation described above can be carried out where the feeding rate of phosphorus is limited.

The content of PHB in bacterial cells increases as the feeding rate of phosphorus is reduced and the retention time in a fermentation vessel is extended. When the retention time is chosen to be more than 10 hours, a great increase in the content of PHB is observed. To make the retention time more than 10 hours, the feeding molar ratio of carbon atom to phosphorus atom (C/P ratio) is usually adjusted to more than 500. The carbon atom of C/P ratio is derived from methanol and the phosphorus atom of C/P ratio is derived from phosphorus source such as phosphoric acid.

[Fermentation method where feeding of potassium is limited]

While the source of potassium is generally fed as a mixture with other components of the fermentation medium which are fed continuously, it can be fed at a constant rate separately from other components of the fermentation medium which are continuously fed. Thus, a fermentation method can be undertaken where the amount of the potassium source is reduced to the amount less than that required for bacterial cells to actively grow, namely, potassium feeding rate is limited such that the potassium feeding rate is a limiting factor for the growth of bacterial cells.

Determination of the concentration of residual potassium in the fermentation broth is continuously carried out by a conventional method with an ion chromatography, as the concentration of potassium ion (Determination is possible down to 1 ppm). According to the fermentation method of the present invention, the amount of potassium ion becomes such a low level that potassium ion can not be detected substantially. However, when the mixing property of the fermentation broth is bad, the concentration of residual potassium ion in the fermentation broth may show a few ppm in partial.

In this fermentation method, fermentation is undertaken while keeping a stationary state by limiting the feeding rate of potassium to a fermentation vessel. Thus, this fermentation method, the growth limiting factor is only potassium.

After the fermentation was switched to a continuous fermentation of the present invention, the feeding of a potassium source is controlled such that the concentration of residual potassium in the fermentation broth is decreased to such a low level that the amount of potassium ion can not be detected by an ion analyzer usually employed. At the same time, the feeding amount of the fermentation medium or methanol is controlled such that the concentration of residual methanol in the fermentation broth is constant. In the production in commercial scale, the feeding amount of methanol and fermentation medium is automatically adjusted by determining the concentration of residual methanol with the passage of time by with an analyzer such as a gas chromatography, and feeding back the signals from the analyzer to the feeding system of methanol or medium.

The concentration of residual methanol in the fermentation broth is maintained usually about 10 to about 3,000 ppm and preferably about 200 to about 2,000 ppm.

The concentration of the residual methanol can also be found by determining the amount of methanol in a fermentation waste gas with an analyzer such as a hydrocarbon analyzer or a gas chromatography.

Thus, a stationary state in the fermentation can be obtained under a constant aeration condition, and it is only potassium which restrict the growth of bacterium under the stationary state.

While the concentration of bacterial cells in the fermentation broth of a continuous fermentation of the present invention is not particularly restricted, it is usually 10 to 100 g/l. The preliminary fermentation is shifted to a continuous fermentation of the present invention after the concentration of bacterial cells of the preliminary fermentation reached about the same concentration as that of bacterial cells at a stationary state of the present invention or slightly lower concentration.

The growth rate of a bacterium can be arbitrarily varied by adjusting the feeding rate of potassium. That is, in order to increase the growth rate (to shorten the retention time), conditions which increase the feeding rate of potassium can be satisfactorily selected. Conversely, in order to reduce the growth rate (to increase the retention time), conditions which decrease the feeding rate of potassium can be acceptably selected.

Prior to a continuous fermentation to be conducted under a limitation of potassium feeding rate in the present invention, a preliminary fermentation is undertaken where a bacterium is actively grown until the concentration of the bacterium in the fermentation broth reaches a prescribed value.

The preliminary fermentation includes, for example, a batch fermentation where a fermentation is undertaken while feeding a sufficient amount of a substrate, other components of the fermentation medium, and oxygen; another batch fermentation where fermentation is undertaken while limiting the feeding of only potassium; and a continuous fermentation where a continuous fermentation is undertaken while feeding a sufficient amount of a substrate, other components of the fermentation medium, and potassium, following such a batch fermentation as mentioned above.

The preliminary fermentation can be undertaken by a usual method, and fermentation temperature, pH, type of substrate, components of the fermentation medium, concentration of a substrate in the medium or fermentation broth are the same as those in a continuous fermentation of the present invention.

Following the preliminary fermentation, the continuous fermentation described above can be carried out where the feeding rate of potassium is limited.

The content of PHB in bacterial cells increases as the feeding rate of potassium is reduced and the retention time in a fermentation vessel is extended. When the retention time is chosen to be more than 10 hours, a great increase in the content of PHB is observed. To make the retention time more than 10 hours, the feeding molar ratio of carbon atom to potassium atom (C/K ratio) is usually adjusted to more than 800. The carbon atom of C/K ratio is derived from methanol and the potassium atom of C/K ratio is derived from potassium source such as caustic potash.

Bacterial cells can be separated and collected from the fermentation broth obtained by fermenting bacterial cells while limiting the feeding of nitrogen, phosphorus, or potassium, by a usual solid-liquid separation method such as filtration and centrifugation, followed by washing with, for example, water as necessary.

PHB can be separated, for instance, by such a known procedure mentioned blow, from the bacterial cells thus obtained or bacterial cells which were broken by subjecting the cells further to an ultrasonic treatment, as desired.

That is, PHB can be separated from a PHB extract obtained by extracting from bacterial cells mentioned above with a halogenated hydrocarbon such as chloroform and 1,2-dichloroethane as an extracting liquid, then by mixing with a poor solvent to precipitate PHB.

Besides, PHB having a high purity can be obtained by subjecting the PHB further to a purification treatment.

In the process of the present invention, a great labour saving, compared with conventional processes where batch fermentations are repeated, can be achieved, since a poly-3-hydroxy butyric acid is produced by a continuous fermentation of the present invention. Since a raw material is methanol, raw material cost is low and there is no fear of contamination by saprophytes in the process of the present invention. Thus, according to the present invention, a poly-3-hydroxy butyric acid can be produced in a large scale, and economically and stably.

EXAMPLES

Now, the present invention will be described in further detail with reference to Examples. However, it should be understood that the present invention is by no means restricted by such specific Examples.

Example 1

*Protomonas extorquens* K (FERM-BP 3548) was used.

According to the following literatures both lately published, *Protomonas extorquens* K (FERM-BP 3548) is considered to belong to a genus of Methylobacterium;

I. J. Bousfield and P. N. Green; Int. J. Syst. Bacteriol., 35, 209 (1985) and

T. Urakami et al.; Int. J. Syst. Bacteriol., 43,504–513 (1993).

The fermentation medium (Medium A) for batch fermentation having the following composition per 1 liter of water was prepared:

| Composition of medium for batch fermentation (Medium A) | |
| --- | --- |
| Methanol | 5 g |
| $KH_2PO_4$ | 3 g |
| $(NH_4)_2SO_4$ | 1 g |
| $MgSO_4.7H_2O$ | 1 g |
| Yeast extract | 0.2 g |
| $FeC_6H_5O_7.xH_2O$ | 60 mg |
| $ZnSO_4.7H_2O$ | 20 mg |
| $MnCl_2.4H_2O$ | 10 mg |
| $CaCl_2.2H_2O$ | 40 mg |
| $CuSO_4.5H_2O$ | 1 mg |
| KI | 1 mg |
| $(NH_4)_6Mo_7O_{24}.4H_2O$ | 1 mg |
| $COCl_2.6H_2O$ | 1 mg |
| $H_3BO_3$ | 1 mg |
| NaCl | 50 mg |

To a fermentation vessel (fermenter) having a volume of 3 liter was placed 1.5 liter of the Medium A.

After the Medium A was heated at 120° C. for 20 min for sterilization and cooled, the pH of the Medium A was adjusted to 6.5 with an aqueous ammonia.

To this fermentation medium was inoculated 200 ml of seed culture prepared in a separate step and subjected to a batch fermentation at 32° C. while aerating with air. The pH of the batch fermentation broth was automatically adjusted to 6.5 with a 25% aqueous ammonia.

The concentration of methanol in the fermentation broth was continuously determined by a gas chromatography, and methanol was automatically fed such that the methanol concentration in the fermentation broth was in a range of 500 to 1,500 ppm.

The agitation speed was adjusted to 1,000 rpm and the aeration rate was adjusted to 1 vvm.

When the concentration of bacterial cells reached about 15 g/l, the 25% aqueous ammonia for pH control was switched to a 25% caustic soda, the feeding of methanol was stopped, and the continuous feeding of a medium for continuous fermentation (Medium B) prepared in a separate step and the continuous discharge of the fermentation broth were started for shifting the procedure to a continuous fermentation.

The composition of the medium for the continuous fermentation is described below, and the medium was used after it was heated at 120° C. for 20 min for sterilization and then cooled. However, methanol was introduced aseptically after it was filtered with a microfilter in order to remove microorganisms.

| Composition of medium for continuous fermentation (Medium B) | per 1 liter of water |
| --- | --- |
| Methanol | 120 g |
| $KH_2PO_4$ | 6 g |
| $MgSO_4.7H_2O$ | 2 g |
| $(NH_4)_2SO_4$ | 1 g |
| $FeC_6H_5O_7.xH_2O$ | 120 mg |
| $ZnSO_4.7H_2O$ | 40 mg |
| $MnCl_2.4H_2O$ | 20 mg |
| $CaCl_2.2H_2O$ | 80 mg |

11
-continued

| Composition of medium for continuous fermentation (Medium B) | per 1 liter of water |
|---|---|
| CuSO$_4$.5H$_2$O | 2 mg |
| KI | 2 mg |
| (NH$_4$)$_6$Mo$_7$O$_{24}$.4H$_2$O | 2 mg |
| CoCl$_2$.6H$_2$O | 2 mg |
| H$_3$BO$_3$ | 2 mg |
| NaCl | 100 mg |
| Defoaming agent (Silicone KM-75) | 2 g |

An aqueous ammonia of 25% concentration was continuously fed concurrently with the feeding of the medium for a continuous fermentation.

The feeding rate of the aqueous ammonia was linked to that of methanol which was supplied as a medium for continuous fermentation. Specifically, the aqueous ammonia was fed at such a rate that the feeding molar ratio of methanol to ammonia was 25. The concentration of methanol in the fermentation broth was reduced as much as possible to decrease the loss of methanol and it was specifically controlled to 300 to 500 ppm.

The concentration of ammonium ion in the fermentation broth was continuously determined by an ion chromatography.

After it was shifted to a continuous fermentation, the concentration of ammonium ion was gradually decreased and shortly the concentration became a value lower than a detection limit (1 ppm).

Under this condition, the fermentation became a stationary state with a retention time of about 40 hours. While the fermentation was continued for 10 days under this condition, the results of the fermentation were stable.

At this time, bacterial cells which contained about 57% of PHB existed in the fermentation broth, in an amount of 42 g per 1 liter of the broth.

The yield of bacterial cells and that of PHB per 1 g of methanol were 0.35 g and 0.20 g, respectively.

Thereafter, the retention time was changed by changing the ammonia feeding rate, and the relationship between the retention time and the content of PHB was investigated. The results thus obtained are shown in Table 1 below.

The analysis of PHB was carried out by the procedures as follows:

After bacterial cells were collected with a centrifugal separator, they were washed twice with pure water and dried with a heated air at 100° C. to obtain dried bacterial cells.

About 80 mg of the dried bacterial cells were taken into a test tube provided with a screw cap, added with 1 ml of chloroform and 1 ml of a methanol-sulfuric acid solution containing an internal standard (Internal standard: benzoic acid 200 mg/100 ml, sulfuric acid 3.5% by volume), and then subjected to a heat treatment at 120° C. for 90 min for degradation and methyl esterification of the polymer contained in the bacterial cells.

After the reaction was over, 1 ml of pure water was added. The mixture was stirred vigorously, and then centrifuged to obtain an organic solvent layer.

The organic solvent layer was analyzed by a gas chromatography under the following conditions and the content of PHB component was calculated:

Analytical conditions for gas chromatography:
Apparatus: Shimadzu GC-7AG

12

Column: Reoplex 400 Chromosorb G AW-DMCS 10% (60–80 mesh)

Column temperature: 160° C.

Inlet temperature: 250° C.

TABLE 1

| Retention time (hr) | Content of PHB (%) | Yield of bacterial cells based on methanol (g/g) | Yield of PHB based on methanol (g/g) |
|---|---|---|---|
| 10 | 14 | 0.36 | 0.05 |
| 15 | 32 | 0.36 | 0.12 |
| 20 | 40 | 0.35 | 0.14 |
| 40 | 57 | 0.35 | 0.20 |
| 65 | 65 | 0.36 | 0.23 |

Table 1 shows the relationship of the retention time with the content of PHB in the bacterial cells, yield of bacterial cells based on methanol, and PHB yield based on methanol, respectively. From Table 1, it can be understood that the content of PHB in the bacterial cells increases as the retention time is extended and when the retention time was chosen to be more than 15 hours, PHB content remarkably increases in the nitrogen-limiting continuous fermentation of the present invention.

Comparative Example 1

Experiments were conducted in the ways similar to those in Example 1 to ferment bacteria except the followings:

The nitrogen-limiting continuous fermentation was changed to a substrate-limiting continuous fermentation where the feeding of methanol was limited;

The caustic soda used for pH-control at the continuous fermentation was changed to an aqueous ammonia and thus the feeding of nitrogen was not limited; and The retention time was changed by changing the feeding rate of the medium.

When the retention time was chosen to be 40 hours, the content of PHB was 0%. At this time, the concentration of ammonium ion in the fermentation broth was 800 to 1,000 ppm. Methanol was not detected in the fermentation broth.

While the retention time was varied by changing the feeding rate of the medium to investigate the relationship between the retention time and PHB content, the content of PHB was as low as 0 to 7% in each of the conditions in this Example.

Example 2

Protomonas extorquens K (FERM-BP 3548) was used.

To a fermentation vessel having a volume of 3 liter was placed 1.5 liter of the Medium A. Then, the Medium A was heated at 120° C. for 20 min for sterilization and cooled, and the pH of the fermentation medium was adjusted to 6.5 with an aqueous ammonia.

To this medium was inoculated 200 ml of seed culture prepared in a separate step and subjected to a batch fermentation at 33° C. while aerating with air. The pH of the batch fermentation broth was automatically adjusted to 6.5 with a 25% aqueous ammonia.

The concentration of methanol in the fermentation broth was continuously determined by a gas chromatography, and methanol was automatically fed such that the methanol concentration in the fermentation broth was in a range of 500 to 1,500 ppm.

The agitation speed was adjusted to 1,450 rpm and the aeration rate was adjusted to 1 vvm.

When the concentration of bacterial cells reached about 10 g/l, the 25% aqueous ammonia for pH control was switched to a 25% caustic soda, and the continuous feeding of a medium for continuous fermentation (Medium C) which was prepared in a separate step and contained 10 g/l of $(NH_4)_2SO_4$, and the continuous discharge of the fermentation broth were started for shifting the procedure to a continuous fermentation.

Methanol was, however, automatically fed separately from the Medium C as it was at the step for batch fermentation.

Polypropylene glycol was added as a defoaming agent in an amount of 1% to the methanol.

| Composition of medium for continuous fermentation (Medium C) | per 1 liter of water |
|---|---|
| $KH_2PO_4$ | 6 g |
| $MgSO_4.7H_2O$ | 2 g |
| $(NH_4)_2SO_4$ | 10 g |
| $FeC_6H_5O_7 \cdot xH_2O$ | 120 mg |
| $ZnSO_4.7H_2O$ | 40 mg |
| $MnCl_2.4H_2O$ | 20 mg |
| $CaCl_2.2H_2O$ | 80 mg |
| $CuSO_4.5H_2O$ | 2 mg |
| KI | 2 mg |
| $(NH_4)_6Mo_7O_{24}.4H_2O$ | 2 mg |
| $CoCl_2.6H_2O$ | 2 mg |
| $H_3BO_3$ | 2 mg |
| NaCl | 100 mg |

The feeding rate of the medium was adjusted such that the retention time was 40 hours.

The concentration of methanol in the fermentation broth was reduced as much as possible to decrease the loss of methanol and it was specifically controlled to 300 to 500 ppm.

The concentration of ammonium ion in the fermentation broth was continuously determined by an ion chromatography.

After it was shifted to a continuous fermentation, the concentration of ammonium ion was gradually decreased and shortly the concentration became a value lower than a detection limit (1 ppm).

Under this condition, the fermentation became a stationary state with a retention time of about 40 hours. At this time, the feeding rate of methanol and that of ammonium ion which was fed as a medium for the continuous fermentation was 25 in terms of the C/N ratio.

While the fermentation was continued for 10 days under this condition, the results of the fermentation were stable. At this time, bacterial cells which contained about 60% of PHB existed in the fermentation broth, in an amount of 43.2 g per 1 liter of the broth.

The yield of bacterial cells and PHB per 1 g of methanol were 0.36 g and 0.22 g, respectively.

Example 3

Example 1 was repeated except that *Hyphomicrobium methylovorum* IFO 14180 was used as strain. The results are shown in Table 2.

Example 4

Example 1 was repeated except that *Hyphomicrobium hollandicum* ATCC 27498 was used as strain. The results are shown in Table 2.

Example 5

Example 1 was repeated except that *Methylobacterium rhodesianum* ATCC 21611 was used as strain. The results are shown in Table 2.

Example 6

Example 1 was repeated except that *Paracoccus denitrificans* DSM 1403 was used as strain. The results are shown in Table 2.

TABLE 2

| Strain | Retention time (hr) | Concentration of bacterial cells (g/l) | Content of PHB (%) |
|---|---|---|---|
| IFO 14180 | 37.2 | 45.1 | 48.8 |
| ATCC 27498 | 39.7 | 40.6 | 56.7 |
| ATCC 21611 | 37.9 | 34.5 | 43.8 |
| DSM 1403 | 43.2 | 39.6 | 40.2 |

| Strain | Yield of bacterial cells based on methanol (g/g) | Yield of PHB based on methanol (g/g) |
|---|---|---|
| IFO 14180 | 0.38 | 0.18 |
| ATCC 27498 | 0.34 | 0.19 |
| ATCC 21611 | 0.29 | 0.13 |
| DSM 1403 | 0.33 | 0.13 |

Example 7

*Protomonas extorquens* K (FERM-BP 3548) was used.

To a fermentation vessel having a volume of 30 liter was placed 15 liter of the the same Medium A as in Example 1.

After the Medium A was heated at 120° C. for 20 min for sterilization and cooled, the pH of the fermentation medium was adjusted to 6.5 with an aqueous ammonia.

To this medium was inoculated 200 ml of seed culture prepared in a separate step and subjected to a batch fermentation at 33° C. while aerating with air. The pH of the batch fermentation was automatically adjusted to 6.5 with a 25% aqueous ammonia.

The concentration of methanol in the fermentation broth was continuously calculated from the value obtained by waste gas by a hydrocarbon analyzer, and methanol was automatically fed such that the methanol concentration in the fermentation broth was in a range of 500 to 1,500 ppm.

The agitation speed was adjusted to 800 rpm and the aeration rate was adjusted to 1 vvm.

When the concentration of bacterial cells reached about 15 g/l, the 25% aqueous ammonia for pH control was switched to a 25% caustic soda, feeding of methanol was stopped, and the continuous feeding of the same medium for continuous fermentation (Medium B) as in Example 1 and the continuous discharge of the fermentation broth were started for shifting the procedure to a continuous fermentation.

An aqueous ammonia of 25% concentration was continuously fed concurrently with the feeding of the medium for a continuous fermentation.

The feeding rate of the aqueous ammonia was linked to that of methanol which was fed as a medium for continuous fermentation such that the C/N ratio was 25. The concentration of methanol in the fermentation broth was reduced as much as possible to decrease the loss of methanol and specifically it was controlled to 300 to 500 ppm.

The concentration of ammonium ion in the fermentation broth was continuously determined by an ion chromatography.

After it was shifted to a continuous fermentation, the concentration of ammonium ion was gradually decreased and shortly the concentration became a value lower than a detection limit (1 ppm).

Under this condition, the fermentation became a stationary state with a retention time of about 40 hours.

At this time, bacterial cells which contained about 55% of PHB existed in the fermentation broth, in an amount of 40 g per 1 liter of the broth.

The fermentation was further continued for 40 days under this condition. As a result, the content of PHB and the concentration of bacterial cells showed a tendency to gradually increase with the passage of the fermentation. After passage of 20 days, the content of PHB was 62% and the concentration of the bacterial cells was 45 g/l. After the passage of 40 days, the content of PHB was 65% and the concentration of the bacterial cells was 47 g/l. At this time, the yield of bacterial cells and that of PHB per 1 g of methanol were 0.39 g and 0.25 g, respectively.

Example 8

*Protomonas extorquens* K (FERM-BP 3548) was used.

The same medium for batch fermentation (Medium A) as in Example 1 was prepared. This medium was placed in a fermentation vessel having a volume of 3 liter.

After the Medium A was heated at 120° C. for 20 min for sterilization and cooled, the pH of the fermentation medium was adjusted to 6.5 with an aqueous ammonia.

To this medium was inoculated 200 ml of seed culture prepared in a separate step and subjected to a batch fermentation at 32° C. while aerating with air. The pH of the batch fermentation broth was automatically adjusted to 6.5 with a 25% aqueous ammonia.

The concentration of methanol in the fermentation broth was continuously determined by a gas chromatography and methanol was automatically fed such that the methanol concentration in the fermentation broth was in a range of 500 to 1,500 ppm.

The agitation speed was adjusted to 1,000 rpm and the aeration rate was adjusted to 1 vvm.

When the concentration of bacterial cells reached about 10 g/l, the methanol which was automatically fed was switched to a medium for continuous fermentation (Medium D) which was prepared in a separate step, and the continuous feeding of the medium and the continuous discharge of the fermentation broth were started for shifting the procedure to a continuous fermentation.

The composition of the medium for the continuous fermentation is described below, and the medium was used after it was heated at 120° C. for 20 min for sterilization and then cooled. However, methanol was introduced aseptically after it was subjected to filtration with a microfilter in order to remove microorganisms.

| Composition of medium for continuous fermentation (Medium D) | per 1 liter of water |
|---|---|
| Methanol | 60 g |
| $K_2SO_4$ | 0.8 g |

| Composition of medium for continuous fermentation (Medium D) | per 1 liter of water |
|---|---|
| $MgSO_4.7H_2O$ | 1 g |
| $(NH_4)_2SO_4$ | 0.5 g |
| $FeC_6H_5O_7.xH_2O$ | 60 mg |
| $ZnSO_4.7H_2O$ | 20 mg |
| $MnCl_2.4H_2O$ | 10 mg |
| $CaCl_2.2H_2O$ | 40 mg |
| $CuSO_4.5H_2O$ | 1 mg |
| KI | 1 mg |
| $(NH_4)_6Mo_7O_{24}.4H_2O$ | 1 mg |
| $CoCl_2.6H_2O$ | 1 mg |
| $H_3BO_3$ | 1 mg |
| NaCl | 50 mg |
| Defoaming agent (Silicone KM-75) | 1 g |

Concurrently with the feeding of the medium for a continuous fermentation, a 10% phosphoric acid solution was continuously fed.

The feeding rate of the 10% phosphoric acid solution was linked to that of methanol which was fed as a medium for continuous fermentation such that a feeding molar ratio of methanol to phosphoric acid was 1,000 in terms of the C/P ratio.

The concentration of methanol in the fermentation broth was reduced as much as possible in order to decrease the loss of methanol and specifically it was controlled to 300 to 500 ppm.

The concentration of phosphoric acid ion in the fermentation broth was continuously determined by an ion chromatography.

After it was shifted to a continuous fermentation, the concentration of phosphoric acid ion was gradually decreased and shortly concentration became a value lower than a detection limit (1 ppm).

Under this condition, the fermentation became a stationary state with a retention time of about 20 hours. While the fermentation was continued for 10 days under this condition, the results of the fermentation were stable.

At this time, bacterial cells which contained about 42% of PHB existed in the fermentation broth, in an amount of 25 g per 1 liter of the broth.

The yield of the bacterial cells and PHB per 1 g of methanol was 0.42 g and 0.18 g, respectively.

Thereafter, the relationship between the retention time and the content of PHB was investigated by changing the retention time, which was effected by varying the feeding rate of phosphoric acid (that is, by changing the C/P ratio). The results are shown in Table 3.

TABLE 3

| Retention time (hr) | Content of PHB (%) | Yield of bacterial cells based on methanol (g/g) | Yield of PHB based on methanol (g/g) |
|---|---|---|---|
| 7 | 17 | 0.41 | 0.07 |
| 10 | 30 | 0.41 | 0.12 |
| 20 | 42 | 0.42 | 0.18 |
| 30 | 49 | 0.42 | 0.21 |
| 40· | 53 | 0.38 | 0.20 |

Table 3 shows the relationship of the retention time with the content of PHB in the bacterial cells, the yield of bacterial cells based on methanol, and the PHB yield based on methanol, respectively. From Table 3, it can be understood that the content of PHB in the bacterial cells increases as the retention time is extended and when the retention time was chosen to be more than 10 hours, PHB content remarkably increases in the phosphorus-limiting continuous fermentation of the present invention.

Example 9

*Protomonas extorquens* K (FERM-BP 3548) was used.

The same medium for batch fermentation (Medium A) as in Example 1 was placed in a fermentation vessel having a volume of 3 liter.

After the Medium A was heated at 120° C. for 20 min for sterilization and cooled, the pH of the fermentation medium was adjusted to 6.5 with an aqueous ammonia.

To this solution was inoculated 200 ml of seed culture prepared in a separate step and subjected to a batch fermentation at 33° C. while aerating with air. The pH of the batch fermentation broth was automatically adjusted to 6.5 with a 25% aqueous ammonia.

The concentration of methanol in the fermentation broth was continuously determined by a gas chromatography and methanol was automatically fed such that the methanol concentration in the fermentation broth was in a range of 500 to 1,500 ppm.

The agitation speed was adjusted to 1,450 rpm and the aeration rate was adjusted to 1 vvm.

When the concentration of bacterial cells reached about 15 g/l, continuous feeding of the following medium for continuous fermentation (Medium E) which was prepared in a separate step and contained 0.22 g/l of $H_3PO_4$ and continuous discharge of the fermentation solution were started for shifting the procedure to a continuous fermentation.

Methanol was, however, automatically fed separately from the Medium E at the feeding rate being linked to that of the medium E.

Polypropylene glycol was added as a defoaming agent in an amount of 1% to the methanol.

| Composition of medium for continuous fermentation (Medium E) | per 1 liter of water |
|---|---|
| $H_3PO_4$ | 0.22 g |
| $K_2SO_4$ | 1.5 g |
| $MgSO_4.7H_2O$ | 2 g |
| $(NH_4)_2SO_4$ | 1 g |
| $FeC_6H_5O_7.xH_2O$ | 120 mg |
| $ZnSO_4.7H_2O$ | 40 mg |
| $MnCl_2.4H_2O$ | 20 mg |
| $CaCl_2.2H_2O$ | 80 mg |
| $CuSO_4.5H_2O$ | 2 mg |
| KI | 2 mg |
| $(NH_4)_6Mo_7O_{24}.4H_2O$ | 2 mg |
| $CoCl_2.6H_2O$ | 2 mg |
| $H_3BO_3$ | 2 mg |
| NaCl | 100 mg |

The feeding rate of the medium was adjusted such that the retention time was 40 hours.

The concentration of residual methanol in the fermentation broth was reduced as much as possible in order to decrease the loss of methanol and it was specifically controlled to 300 to 500 ppm.

The concentration of phosphoric acid ion in the fermentation broth was continuously determined by an ion chromatography.

After it was shifted to a continuous fermentation, the concentration of phosphoric acid ion was gradually decreased and shortly the concentration became a value lower than a detection limit (1 ppm).

Under this condition, the fermentation became a stationary state with the retention time of about 40 hours.

At this time, the feeding rate of methanol and that of phosphoric acid ion which was fed as a medium for continuous fermentation was 1670 in terms of the C/P ratio.

While the fermentation was continued for 10 days under this condition, the results of the fermentation were stable.

At this time, bacterial cells which contained about 53% of PHB existed in the fermentation broth, in an amount of 45.6 g per 1 liter of the broth.

The yield of the bacterial cells and PHB per 1 g of methanol were 0.38 g and 0.20 g, respectively.

Example 10

Example 8 was repeated except that *Hyphomicrobium methylovorum* IFO 14180 was used as strain.

After it was shifted to continuous fermentation, fermentation became a stationary state with the retention time of about 20 hours.

While the fermentation was continued for 10 days under this condition, the results of the fermentation were stable.

At this time, bacterial cells which contained about 48% of PHB existed in the fermentation broth, in an amount of 27 g per 1 liter of the broth.

The yield of bacterial cells and PHB per 1 g of methanol were 0.45 g and 0.22 g, respectively.

Example 11

*Protomonas extorquens* K (FERM-BP 3548) was used.

The same medium for batch fermentation (Medium A) as in Example 1 was prepared. This medium in an amount of 1.5 liter was placed in a fermentation vessel having a volume of 3 liter.

After the Medium A was heated at 120° C. for 20 min for sterilization and cooled, the pH of the fermentation medium was adjusted to 6.5 with an aqueous ammonia.

To this medium was inoculated 200 ml of seed culture prepared in a separate step and subjected to a batch fermentation at 32° C. while aerating with air. The pH of the batch fermentation broth was automatically adjusted to 6.5 with a 25% aqueous ammonia.

The concentration of methanol in the fermentation broth was continuously determined by a gas chromatography and methanol was automatically fed such that the methanol concentration in the fermentation broth was in a range of 500 to 1,500 ppm.

The agitation speed was adjusted to 1,000 rpm and the aeration rate was adjusted to 1 vvm.

When the concentration of bacterial cells reached about 10 g/l, the methanol which was automatically fed during preliminary fementation was switched to a medium for continuous fermentation (Medium F) which was prepared in a separate step, and the continuous feeding of the medium and the continuous discharge of the fermentation broth were started for shifting the procedure to a continuous fermentation.

The pH of the fermentation broth was continuously controlled to 6.5 with a 25% aqueous ammonia as it was at the batch fermentation.

The composition of the medium for the continuous fermentation is described below, and the medium was used after it was heated at 120° C. for 20 min for sterilization and then cooled. However, methanol was introduced aseptically after it was filtered with a microfilter in order to remove microorganisms.

| Composition of medium for continuous fermentation (Medium F) | per 1 liter of water |
|---|---|
| Methanol | 60 g |
| $H_3PO_4$ | 1.5 g |
| $MgSO_4.7H_2O$ | 1 g |
| $(NH_4)_2SO_4$ | 0.5 g |
| $FeC_6H_5O_7.xH_2O$ | 60 mg |
| $ZnSO_4.7H_2O$ | 20 mg |
| $MnCl_2.4H_2O$ | 10 mg |
| $CaCl_2.2H_2O$ | 40 mg |
| $CuSO_4.5H_2O$ | 1 mg |
| KI | 1 mg |
| $(NH_4)_6Mo_7O_{24}.4H_2O$ | 1 mg |
| $CoCl_2.6H_2O$ | 1 mg |
| $H_3BO_3$ | 1 mg |
| NaCl | 50 mg |
| Defoaming agent (Silicone KM-75) | 1 g |

Concurrently with the feeding of the medium for a continuous fermentation, a 10% caustic potash solution was continuously fed.

The feeding rate of the 10% caustic potash solution was linked to that of methanol which was fed as a medium for continuous fermentation such that a feeding molar ratio of methanol to caustic potash was 1,700 in terms of the C/K ratio.

The concentration of methanol in the fermentation broth was reduced as much as possible in order to decrease the loss of methanol and specifically controlled to 300 to 500 ppm.

The concentration of potassium ion in the fermentation broth was continuously determined by an ion chromatography.

After it was shifted to a continuous fermentation, the concentration of potassium ion was gradually decreased and shortly the concentration became a value lower than a detection limit (1 ppm).

Under this condition, the fermentation became a stationary state with a retention time of about 20 hours. While the fermentation was continued for 10 days under this condition, the results of the fermentation were stable.

At this time, bacterial cells which contained about 51% of PHB existed in the fermentation broth, in an amount of 21 g per 1 liter of the broth.

The yield of the bacterial cells and PHB per 1 g of methanol were 0.35 g and 0.18 g, respectively.

Thereafter, the relationship between the retention time and the content of PHB was investigated by changing the retention time which was effected by varying the feeding rate of caustic potash (that is, by changing the C/K ratio). The results are shown in Table 4.

TABLE 4

| Retention time (hr) | Content of PHB (%) | Yield of bacterial cells based on methanol (g/g) | Yield of PHB based on methanol (g/g) |
|---|---|---|---|
| 7 | 17 | 0.38 | 0.06 |
| 10 | 40 | 0.40 | 0.16 |
| 20 | 51 | 0.35 | 0.18 |
| 30 | 55 | 0.36 | 0.20 |
| 40 | 53 | 0.37 | 0.20 |

Table 4 shows the relationship of the retention time with the content of PHB in the bacterial cells, the yield of bacterial cells based on methanol, and PHB yield based on methanol, respectively. From Table 4, it can be understood that the content of PHB in the bacterial cells increases as the retention time is extended and when the retention time was chosen to be more than 10 hours, PHB content remarkably increases in the potassium-limiting continuous fermentation of the present invention.

Example 12

*Protomonas extorquens* K (FERM-BP 3548) was used.

The same medium for batch fermentation (Medium A) as in Example 1 in an amount of 1.5 liter was placed in a fermentation vessel having a volume of 3 liter.

After the Medium A was heated at 120° C. for 20 min for sterilization and cooled, the pH of the fermentation medium was adjusted to 6.5 with an aqueous ammonia.

To this medium was inoculated 200 ml of seed culture prepared in a separate step and subjected to a batch fermentation at 33° C. while aerating with air. The pH of the batch fermentation broth was automatically adjusted to 6.5 with a 25% aqueous ammonia.

The concentration of methanol in the fermentation broth was continuously determined by a gas chromatography and methanol was automatically fed such that the methanol concentration in the fermentation broth was in a range of 500 to 1,500 ppm.

The agitation speed was adjusted to 1,450 rpm and the aeration rate was adjusted to 1 vvm.

When the concentration of bacterial cells reached about 15 g/l, continuous feeding of the following medium for continuous fermentation (Medium G) which was prepared in a separate step and contained 0.2 g/l of $KH_2PO_4$, and continuous discharge of the fermentation broth were started for shifting the procedure to a continuous fermentation.

Methanol was, however, automatically fed separately from the. Medium G with its feeding rate being linked to that of the Medium G.

Polypropylene glycol was added as a defoaming agent in an amount of 1% to the methanol.

| Composition of medium for continuous fermentation (Medium G) | per 1 liter of water |
|---|---|
| $H_3PO_4$ | 1.5 g |
| $KH_2PO_4$ | 0.2 g |
| $MgSO_4.7H_2O$ | 2 g |
| $(NH_4)_2SO_4$ | 1 g |
| $FeC_6H_5O_7.xH_2O$ | 120 mg |
| $ZnSO_4.7H_2O$ | 40 mg |

| Composition of medium for continuous fermentation (Medium G) | per 1 liter of water |
|---|---|
| $MnCl_2.4H_2O$ | 20 mg |
| $CaCl_2.2H_2O$ | 80 mg |
| $CuSO_4.5H_2O$ | 2 mg |
| KI | 2 mg |
| $(NH_4)_6Mo_7O_{24}.4H_2O$ | 2 mg |
| $COCl_2.6H_2O$ | 2 mg |
| $H_3BO_3$ | 2 mg |
| NaCl | 100 mg |

The feeding rate of the medium was adjusted such that the retention time was 30 hours.

The concentration of residual methanol in the fermentation broth was reduced as much as possible in order to decrease the loss of methanol and it was specifically controlled to 300 to 500 ppm.

The concentration of potassium ion in the fermentation broth was continuously determined by an ion chromatography.

After it was shifted to a continuous fermentation, the concentration of potassium ion was gradually decreased and shortly the concentration became a value lower than a detection limit (1 ppm).

Under this condition, the fermentation became a stationary state with the retention time of about 30 hours.

At this time, the feeding rate of methanol and that of potassium ion which was fed as a medium for continuous fermentation was 2550 in terms of the C/K ratio.

While the fermentation was continued for 10 days under this condition, the results of the fermentation were stable.

At this time, bacterial cells which contained about 56% of PHB existed in the fermentation broth, in an amount of 44.0 g per 1 liter of the broth.

The yield of the bacterial cells and PHB per 1 g of methanol were 0.37 g and 0.21 g, respectively.

Example 13

Example 11 was repeated except that *Hyphomicrobium methylovorum* IFO 14180 was used as strain.

After it was shifted to a continuous fermentation, fermentation became a stationary state with a retention time of about 20 hours.

While the fermentation was further continued for 10 days under this condition, the results of the fermentation were stable.

At this time, bacterial cells which contained about 50% of PHB existed in the fermentation broth, in an amount of 25 g per 1 liter of the broth.

The yield of the bacterial cells and PHB per 1 g of methanol were 0.42 g and 0.21 g, respectively.

We claim:

1. A single stage continuous fermentation process for the production of bacterial cells containing a poly-3-hydroxy burytic acid comprising producing said bacterial cells under the following conditions:

a) using as said bacterial cells a methanol-assimilating bacterium selected from the group consisting of *Protomonas extorquens* K (FERM BP 3548), *Hyphomicrobium methylovorum* (IFO 14180), *Hyphomicrobium hollandism* (IFO 21611 ), *Paracoccus dentrificans* (DSM 1403), and mutants thereof having the ability to produce poly-3-hydroxy butyric acid under the continuous fermentation process conditions herein set forth;

b) using methanol as a source of carbon; and c) undertaking the continuous fermentation at a retention time of more than I 0 hours by limiting the provision of a source of nitrogen, phosphorous, or potassium.

2. The process according to claim 1 wherein the continuous fermentation is undertaken at a retension time of more than 15 hours by limiting the provision of nitrogen source.

3. The process according to claim 1 wherein the continuous fermentation is undertaken at a retension time of more than 10 hours by limiting the provision of phosphorous source.

4. The process according to claim 1 wherein the continuous fermentation is undertaken at a retension time of more than 10 hours by limiting the provision of potassium source.

* * * * *